US011986641B1

(12) United States Patent
Ferraz

(10) Patent No.: US 11,986,641 B1
(45) Date of Patent: May 21, 2024

(54) MICRO-CANNULA AND PILOT NEEDLE MANAGER

(71) Applicant: Adrienne Ferraz, Troy, MI (US)

(72) Inventor: Adrienne Ferraz, Troy, MI (US)

( * ) Notice: Subject to any disclaimer, the term of this patent is extended or adjusted under 35 U.S.C. 154(b) by 216 days.

(21) Appl. No.: 17/691,653

(22) Filed: Mar. 10, 2022

(51) Int. Cl.
*A61M 5/32* (2006.01)
(52) U.S. Cl.
CPC .......... *A61M 5/3202* (2013.01); *A61M 5/321* (2013.01); *A61M 2205/586* (2013.01); *A61M 2209/088* (2013.01)
(58) Field of Classification Search
CPC .............. A61M 5/3202; A61M 5/321; A61M 2205/586; A61M 2209/088; A61M 5/002; A61M 5/008; A61M 5/1418; A61M 5/158; A61M 5/3295; A61M 2005/1416; A61M 2005/1586; A61M 2005/1405; A61M 25/002; A61M 25/02; Y10T 24/1394
See application file for complete search history.

(56) References Cited

U.S. PATENT DOCUMENTS

| | | | | |
|---|---|---|---|---|
| 5,279,578 A * | 1/1994 | Cooke | ................. | A61M 5/3213 604/263 |
| 6,113,577 A * | 9/2000 | Hakky | ................. | A61M 25/02 604/179 |
| 7,255,251 B1 * | 8/2007 | Smith | ................. | A61B 5/15003 604/179 |
| 2003/0057347 A1 * | 3/2003 | Weiss | ................. | A61M 25/00 248/558 |
| 2018/0185025 A1 * | 7/2018 | Gorek | ............... | A61B 17/06061 |

OTHER PUBLICATIONS

"Spider Tool Holster—Magnetic Wrist Wrap—Ergonomic Support Strap Embedded with high Strength Magnets for Carrying Screws, Nails, Drill bits, washers, Sewing Needles—Great Gift for Father, DIY." Amazon. Available since Aug. 12, 2022. Retrieved Mar. 19, 2024. (Year: 2022).*

* cited by examiner

*Primary Examiner* — Tasnim Mehjabin Ahmed
(74) *Attorney, Agent, or Firm* — Christopher J. Vandam, PA; Chris Van Dam

(57) ABSTRACT

A wrist mounted band onto which a clip for an introducer (also known as a pilot needle) in a cap is affixed along with a micro-cannula and a cover. The introducer and micro-cannula are held substantially parallel to the long axis of the wrist band. The attachment points of the introducer and micro-cannula are adjacent on the exterior surface of the band. As the band is wrapped around the wrist the axis of the introducer and micro-cannula become perpendicular to each other and both parallel to the long axis of the band. A user can then store the introducer and its cap affixed to the band and the micro-cannula in its cover affixed to the band at known orientations. The user can then remove and reinstall the introducer and micro-cannula as needed throughout a surgical procedure.

5 Claims, 3 Drawing Sheets

MICRO-CANNULA AND PILOT NEEDLE MANAGER

CROSS-REFERENCES TO RELATED APPLICATIONS

None.

STATEMENT REGARDING FEDERAL SPONSORED RESEARCH OR DEVELOPMENT

None.

NAMES OF PARTIES TO A JOINT RESEARCH AGREEMENT

None.

REFERENCE TO A "SEQUENCE LISTING", A TABLE, OR A COMPUTER PROGRAM LISTING APPENDIX SUBMITTED ON COMPACT DISC AND INCORPORATION-BY-REFERENCE OF THE MATERIAL ON THE COMPACT DISCLOSURE

None.

STATEMENT REGARDING PRIOR DISCLOSURES BY AN INVENTOR OR JOINT INVENTOR

None.

BACKGROUND OF THE INVENTION

1. Field of the Invention

The present invention relates to aesthetic cosmetic procedures, and more particularly, to an improved bracelet to hold a micro-cannula and a pilot needle during a procedure.

2. Description of Related Art Including Information Disclosed Under 37 CFR 1.97 and 37 CFR 1.98

Several designs for sharps holders have been designed in the past. None of them, however, includes a bracelet that safely holds syringe-type implements including micro-cannulas, needles, sharps and introducers in orientations to easily identify the implement, keep the user safe from accidental sticks and maintain sterile tools.

Applicant believes that the closest reference corresponds to commonly used isopropyl alcohol saturated cotton balls used in surgical procedures to hold a needle or introducer. A cotton ball soaked in alcohol is placed on a table near the procedure and the needle tip is placed in the cotton ball to hold it and keep the needle sterile. Other technicians use the plastic caps that protect new needles in the packaging to protect and keep the needles clean.

Other prior art designs include a variety of clips, sleeves, holders and other similar designs that are non-sterile, require two hands to operate and are otherwise not at the user's fingertips during a cosmetic procedure and are therefore cumbersome.

The problem with prior art techniques, such as these, include the high risk of contamination of the needle, high risk of poking the user and an increased risk of dropping a needle during use because of the cumbersome nature of these solutions.

Other patents describing the closest subject matter provide for a number of more or less complicated features fail to solve the problem in an efficient and economical way. None of these patents suggest the novel features of the present invention.

A brief abstract of the technical disclosure in the specification and title are provided as well for the purposes of complying with 37 CFR 1.72 and are not intended to be used for interpreting or limiting the scope of the claims.

Without limiting the scope of the invention, a brief summary of some of the claimed embodiments of the invention is set forth below. Additional details of the summarized embodiments of the invention and/or additional embodiments of the invention may be found in the detailed description of the invention below.

BRIEF SUMMARY OF THE INVENTION

It is one of the main objects of the present invention to provide a pilot needle manager that is conveniently located on a technician's wrist that manages a pilot needle and a micro-cannula.

It is another object of this invention to provide a sterile and secure holder of surgical sharps that can be used with minimal distraction and maximum convenience to the user.

It is still another object of the present invention and to provide a device that reduces contamination of the needles and risk of pricks to the user.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

These and other embodiments which characterize the invention are pointed out with particularity in the claims annexed hereto and form a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE SEVERAL VIEWS OF THE DRAWING

With the above and other related objects in view, the invention exists in the details of construction and combination of parts as will be more fully understood from the following description, when read in conjunction with the accompanying drawings in which.

DETAILED DESCRIPTION OF THE INVENTION

Figure 1:
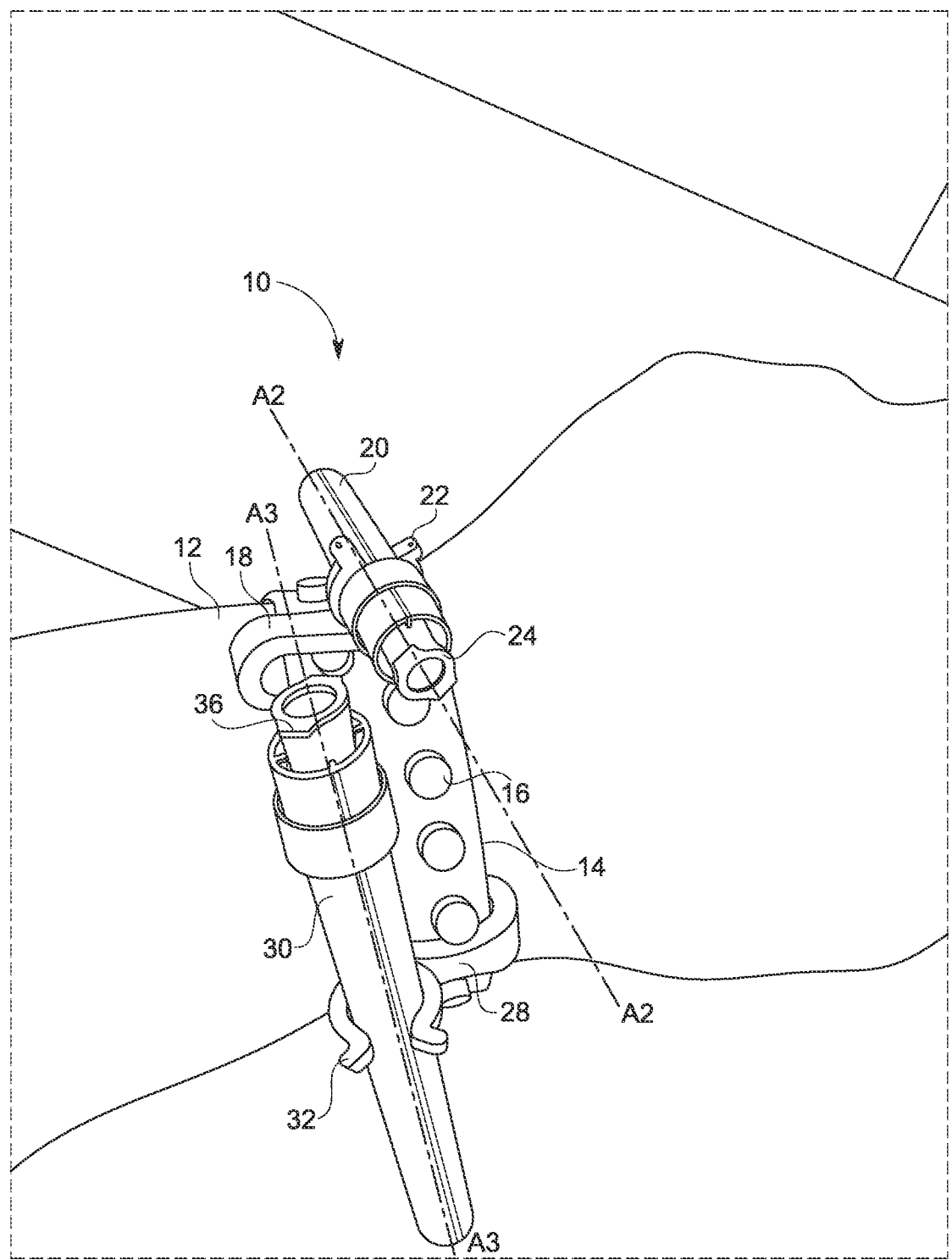
FIG. 1 shows a perspective view of a pilot needle manager attached to a technician's wrist.

While this invention may be embodied in many different forms, there are described in detail herein specific embodiments of the invention. This description is exemplary of the principles of the invention and is not intended to limit the invention to the particular embodiments illustrated and described.

For the purpose of this disclosure, like reference numerals in the figures shall refer to like features unless otherwise indicated or is obvious by context. For the purposes of the specification, the terms needle, pilot needle, hypodermic, introducer and other similar terms are interchangeable, as they relate to the claimed device. The term micro-cannula is generally a blunt tip hollow tube through which liquids and gels are injected under the skin of the patient.

The subject device and method of use is sometimes referred to as the device, the invention, the pilot needle manager, the needle/hypodermic manager, the introducer manager, the micro-cannula manager, the surgical aid, the machine or other similar terms. These terms may be used interchangeably as context requires and from use the intent becomes apparent. The masculine can sometimes refer to the feminine and neuter and vice versa. The plural may include the singular and singular the plural as appropriate from a fair and reasonable interpretation in the situation.

It should be appreciated that the terms pilot needle, hypodermic, sharp and introducer are equivalent terms and represent the same structure. Each has a sharp tip designed to pierce the dermis and provide an aperture through which the micro-cannula is inserted during an aesthetic medical procedure. Commonly the introducer is removed and then the micro-cannula is inserted under the skin. In some adaptations the micro-cannula is fed through the hollow interior of the introducer and under the skin.

Commonly, a micro-cannula is a blunt tipped tube affixed to an injection device to deliver products into the human body. The blunt nature of the micro-cannula is often considered safer because it is less likely to puncture a vessel and deliver the product directly into the bloodstream. However, also due to the blunt tip of the micro-cannula, it is unable to pierce the skin. A sharper tool is required to make the initial perforation.

Generally, a pilot needle and introducer are equivalent terms for a sharp hypodermic-style device used to puncture the dermis during a surgical procedure, such an aesthetic medical procedure. Once the skin is perforated, a micro-cannula is inserted into the tissue below the puncture to deliver a product sub-dermally, such as a dermal filler.

Referring now to the drawings, where the present invention is generally referred to with numeral 10, it can be observed that it basically includes a wrist 12, a band 14, a tab 16, a clip 18, a clip 20, a clip 22, an introducer 24, a clasp 26, a clip 28, a cover 30, a clip 32, an aperture 34, a micro-cannula 36 and axes A1, A2 and A3.

Figure 2:
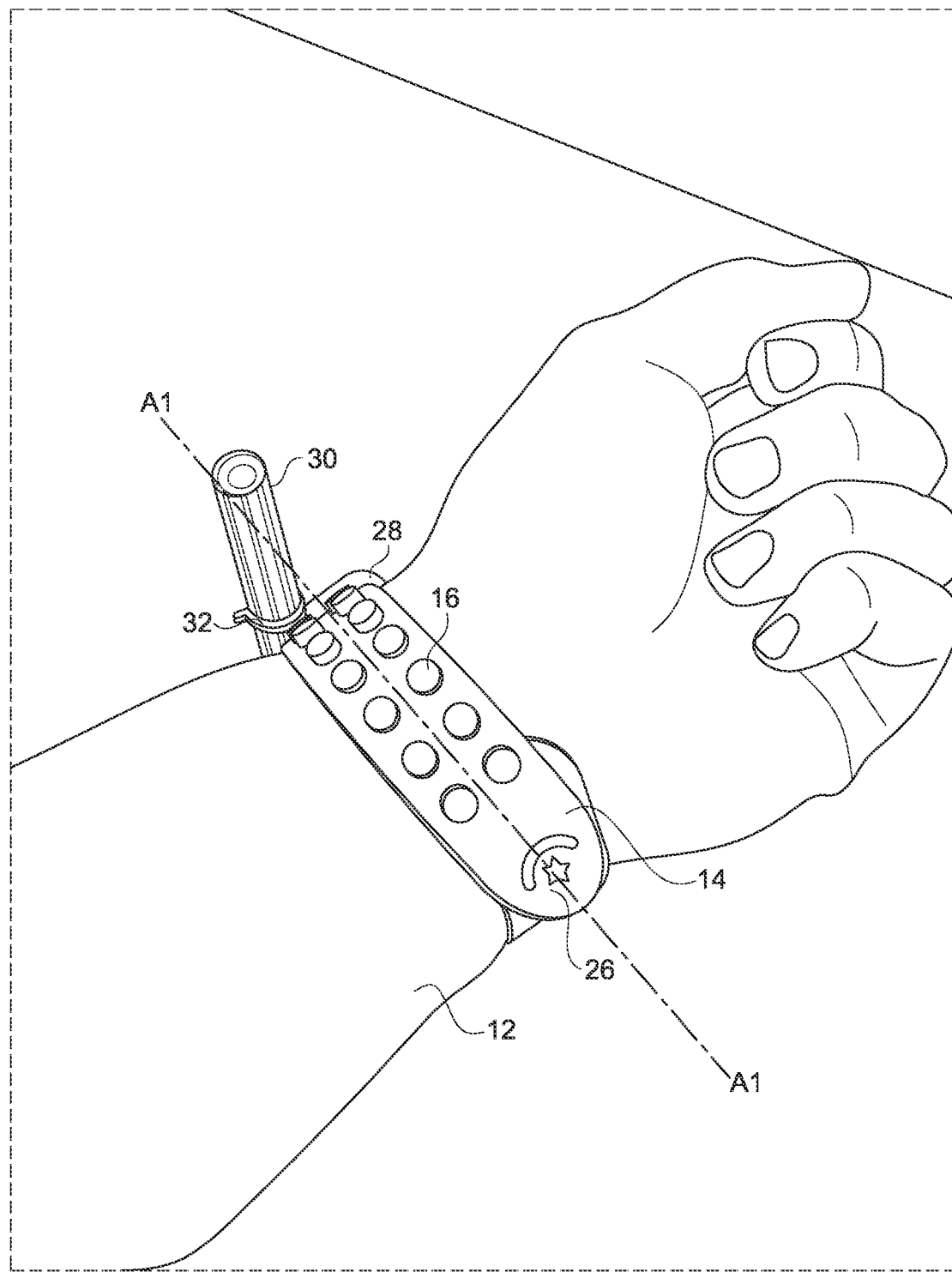
FIG. 2 shows a perspective view of the pilot needle manager below the technician's wrist.
Figure 3:
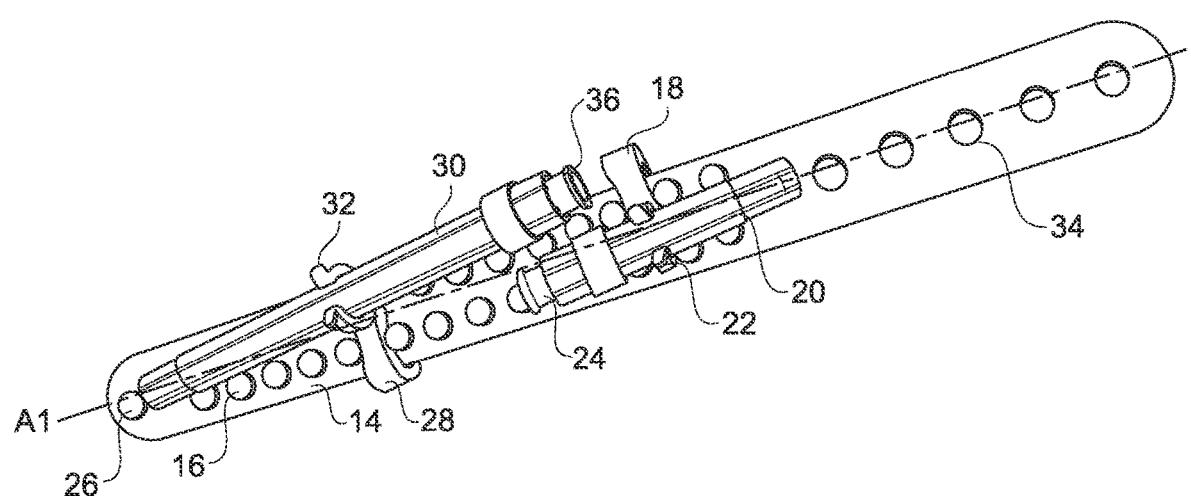
FIG. 3 shows a perspective view of the pilot needle manager laid flat and removed from the technician's wrist.

FIGS. 1, 2 and 3 show an example of a pilot needle manager attached to a technician's wrist. The band 14 wraps around the wrist 12 of the user. A clasp 26 at one end of the band 14 selectively affixes into an aperture 34 on the opposite end of the band to secure the band 14 around the wrist 12 of the user. Multiple apertures 34 may be provided to better fit wrists of different circumferences.

A series of tabs 16 optionally protrude from an exterior surface of the band 14. If present, the tabs 16 help align and keep into place the clip 22 and clip 32. In other versions of the device, there are no tabs 16 or a single row of tabs 16 on the band 14. Alternatively, other protrusions from the exterior surface of the band 14 may be provided perpendicular to axis a one of the band 14.

For example, corrugations in the band 14 that are perpendicular to axis A1 may serve to keep clips 22 or 32 from sliding and will maintain the clips' orientation relative to axis A1. Any structure that aids in keeping the clip 22 and clip 32 perpendicular to axis A1 and in position on the band 14 may be equally used.

The clip 28 attaches to the band 14 by pinching the upper and lower surface of the band a 14. The clip 28 may be removed from the band 14 as needed. Because a clip 28 is removable, it is also replaceable to repair the device or to fit a different size cover 30. Affixed to the clip 28 is clip 32. Clip 32 snaps around the cover 32 hold the cover 30 in place relative to the clip 28.

The cover 30 is dimensioned and adapted to securely fit a surgical tool such as a micro-cannula 36. The cover 30 protects the user from inadvertently being pricked from the micro-cannula 36. Cover 30 also keeps the micro-cannula 36 sterile and sharp while the micro-cannula 36 is presently not in use.

As noted above, prior art storage of micro-cannulas 36 (or introducers 24) included pushing the tip of the micro-cannula 36 into an isopropyl alcohol saturated cotton ball that causes both the tip of the introducer 24 to dull and may also introduce isopropyl alcohol into the interior tip of the micro-cannula 36 or introducer 24 thereby rendering it not-sterile. The tip of the introducer 24 does not touch the interior surfaces of the cover and is therefore protected in perfect condition.

Similar to the micro-cannula 36, the introducer 24 is held safely and sterile inside the cap 20 when the introducer 24 is not in use. The cap 20 is grasped by the clip 22 to maintain the orientation of the long axis of the cap approximately parallel to axis A1. Clip 22 is formed integral with a clip 18. Clip 18 attaches to the band 14 and is removable and replaceable.

The introducer 24 is generally provided from the manufacturer inside the cap 22 to maintain the introducer 24 both sterile and sharp. The introducer 24 friction fits into the cap 22 when fully inserted. A syringe may be threaded onto the base of the introducer 24 to both insert and to remove the introducer 24 from the cap 20. In this way the user of the device never needs to touch any part of the introducer 24. This improves the sterility of the device.

The micro-cannula 36 is provided from the manufacturer inside the cover 32 to maintain sterility and integrity of tip. Similar to other cannulae, the end of the micro-cannula opposite the bunt injection tip is threaded onto a syringe to both insert and remove the micro-cannula 36 from the cover 30 without the user touching the micro-cannula 36 and risking of the sterility of the micro-cannula 36.

In an important embodiment of the device, the combination of clips 28 and 32 and combination of clips 18 and 22 are single piece, plastic devices. Similarly, the cover 30 and 20 are generally constructed of a plastic material. The introducer 24 and micro-cannula 36 are both generally constructed of a hollow metal tube that is attached to a plastic fitting on the opposite end configured with threads to attach to a syringe.

Looking at FIG. 3, the band 14 is laid flat. Axis A1 corresponds with the longer length of band 14. The longer dimension of the cap 20 is shown as axis A2. The longer dimension of cover 30 is shown as axis A3. When the band a 14 is laid flat, axis A1, axis A2 and axis A3 are substantially parallel to each other.

When the band 14 is wrapped around the wrist 12, axis A1 coincides with the circumference of the wrist 12. Due to the spacing between clip 28 and clip 18, axis A2 becomes perpendicular to axis A3 when the band 14 is wrapped around the user's wrist 12. FIG. 1 shows the cap 20 perpendicular to cover 30 when on the user's wrist 12.

This perpendicular aspect between the cap 20 and cover 30 are important for the design of the pilot needle manager. As the user of the device is intently focused on their work in the surgical theater, they can readily determine the difference between the introducer 24 and a micro-cannula 36 based on the orientation of their respective cap 20 and cover 30.

The wearer of the device need only rotate the back of the wrist 12 and they can determine without looking that the introducer 24 is in the horizontal position on the back of the wrist 12 and the clip 32 holding the micro-cannula 36 is positioned vertically along the axis A3. This allows the user of the device to readily transition the syringe from being connected to the introducer 24 to the micro-cannula 36 and back again.

Optionally, the band a 14 is fabricated of a material that is resistant and impervious to piercing by a needle. The band may include a laminate layer that is of a pierce resistant material, such as metal or plastic plates embedded into the material of the band 14. The band 14 should remain flexible to encircle the user's wrist. This can improve the safety of the device to reduce the risk that a user accidentally pokes herself with the introducer or hypodermic.

An important version of the device is fairly characterized as a pilot needle manager comprising a band and to clips. The band has a long axis between a first and the second end of the band. The first clip is affixed to the band and includes an additional integral clip that is affixed to the cap. This clip is configured to orient the cap along an axis that is parallel to the axis of the band. The opening of the cap is oriented toward the first end of the band. This cap holds an introducer in an interior volume of the cap and is friction fit in place. The other clip clips to the band and includes an additional integral clip that is affixed to a cover that holds a micro-cannula parallel to the axis of the band. The micro-cannula is friction fit into the cover. When the band is wrapped around the user's wrist the axis of the first cap and axis of the second cap become perpendicular to each other. The ends of the band are connected to secure around the user's wrist. As the cover and cap are attached to the band, the openings of the cap and cover are adjacent to each other so that as the band wraps around the wrist generally at perpendicular orientations. The cap and cover position the openings of the micro-cannula and introducer near to each other. By having the introducer and micro-cannula perpendicular, the user can readily determine between the two without moving their gaze to visually verify the introducer and microcannula. Optionally, a plurality of tabs are integral to an exterior surface of the band. These are generally perpendicular to the axis of the band and are used to configure both clips attached to the band in a position to retain the respective cap and cover parallel to the axis of the band. The tabs could optionally not be perpendicular to the axis of the band if the clips are otherwise configured to retain the respective can and cover parallel to the axis of the band. Optionally, the tabs are configured on the external surface of the band to prevent either of the clips affixed to the band from sliding axially along the band and also to maintain their relative position on the band. Optionally, the introducer is friction fit into the cap and the micro-cannula is friction fit into the cover to ensure they don't fall from the band during normal use. A syringe barrel or other tool may then be attached to the introducer or micro-cannula to withdraw from the respective cap and cover. Optionally, the band is constructed of a material that prevents needle penetration through the band into the user to improve safety.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

I claim:

1. A micro-cannula and pilot needle manager comprised of a band (14), a first clip (18) and a second clip (28); the band (14) has a long axis (A1) between a first end and a second end;
   the first clip (18) has an integral clip (22) that is affixed to a cap (20); the first clip (18) is affixed to the band (14) and is configured to orient the cap (20) along a second axis (A2) that is parallel to the long axis (A1);
   an opening of the cap (20) is oriented toward the first end of the band (14);
   the cap (20) holds a pilot needle (24) in an interior volume of the cap (20);
   the second clip (28) has an integral clip (32) that is affixed to a cover (30);
   the second clip (28) is affixed to the band (14) and is configured to orient the cover (30) along a third axis (A3) that is parallel to the long axis (A1);
   an opening of the cover (30) is oriented toward the second end of the band (14);
   the cover (30) holds a micro-cannula (36) in an interior volume of the cover (30);
   the band (14) is adapted to be wrapped around a wrist (12) causing the second axis (A2) of the cap (20) to become perpendicular to the third axis (A3) of the cover (30);
   the first end of the band (14) is affixed to the second end of the band (14) securing the band (14).

2. The micro-cannula and pilot needle manager of claim 1 further characterized as a plurality of tabs (16) are integral to an exterior surface of the band (14) that are oriented perpendicular to the long axis (A1) and are configured to retain the first clip (18) and the second clip (28) in position holding the respective cap (20) and cover (30) parallel to the long axis (A1).

3. The micro-cannula and pilot needle manager of claim 2 wherein the tabs (16) are further configured to retain the first clip (18) and the second clip (28) in position to prevent the first clip (18) and the second clip (28) from sliding axially along the long axis (A1).

4. The micro-cannula and pilot needle manager of claim 1 wherein the pilot needle (24) is friction fit into the cap (20) and the micro-cannula (36) is friction fit into the cover (30).

5. The micro-cannula and pilot needle manager of claim 1 wherein the band (14) is constructed of a material impervious to a needle penetration.

* * * * *